US010772643B2

(12) United States Patent
Vipperman et al.

(10) Patent No.: US 10,772,643 B2
(45) Date of Patent: Sep. 15, 2020

(54) SURGICAL TOOL MONITORING SYSTEM AND METHODS OF USE

(71) Applicant: University of Pittsburgh—Of the Commonwealth System of Higher Education, Pittsburgh, PA (US)

(72) Inventors: Jeffrey Vipperman, Pittsburgh, PA (US); Carl Snyderman, Pittsburgh, PA (US); Timothy Ryan, Pittsburgh, PA (US); Paul Johnson, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 225 days.

(21) Appl. No.: 15/964,766

(22) Filed: Apr. 27, 2018

(65) Prior Publication Data
US 2018/0242985 A1    Aug. 30, 2018

Related U.S. Application Data

(62) Division of application No. 14/496,704, filed on Sep. 25, 2014, now Pat. No. 9,980,738.
(Continued)

(51) Int. Cl.
*A61B 17/16*    (2006.01)
*A61B 90/00*    (2016.01)
*A61B 17/00*    (2006.01)

(52) U.S. Cl.
CPC .......... *A61B 17/1695* (2013.01); *A61B 90/06* (2016.02); *A61B 2017/00022* (2013.01);
(Continued)

(58) Field of Classification Search
CPC ................ A61B 17/1695; A61B 90/06; A61B 2017/00022; A61B 2017/00075;
(Continued)

(56) References Cited

U.S. PATENT DOCUMENTS 6,468,274 B1    10/2002    Alleyne et al.
6,579,244 B2    6/2003    Goodwin
(Continued)

FOREIGN PATENT DOCUMENTS

CN    101530341    9/2009
WO    WO 1998/018390    5/1998
WO    WO 2009/117836    10/2009

OTHER PUBLICATIONS

Brady, et al. "The effects of drilling parameters on the acoustic drilling signature of the squamous temporal bone: A categorical multivariate regressive analysis." *Applied Sciences in Biomedical and Communication Technologies (ISABEL)*, 2010 3rd International Symposium on. IEEE, 2010.
(Continued)

*Primary Examiner* — George J Ulsh
(74) *Attorney, Agent, or Firm* — Klarquist Sparkman, LLP

(57) ABSTRACT

A device for simultaneously monitoring the health of surgical drills and detecting proximity to critical structures during surgery is described herein. By using various sensors (e.g. microphones, accelerometers, temperature sensors, etc.), signals from the drill can be measured and analyzed. The processed signals can then be used to indicate the proximity of the drill bit to critical structures, such as the patient's brain, and identify drill health issues (e.g. worn bearings, misaligned rotational axis, etc.).

17 Claims, 6 Drawing Sheets

Related U.S. Application Data

(60) Provisional application No. 61/882,223, filed on Sep. 25, 2013.

(52) U.S. Cl.
CPC ........... *A61B 2017/00075* (2013.01); *A61B 2017/00084* (2013.01); *A61B 2017/00106* (2013.01); *A61B 2017/00119* (2013.01); *A61B 2090/062* (2016.02); *A61B 2090/08021* (2016.02)

(58) Field of Classification Search
CPC ........... A61B 2017/00084; A61B 2017/00106; A61B 2017/00119; A61B 2090/062; A61B 2090/8021; A61C 1/084; A61C 3/02; A61C 5/44; A61C 19/041; A61C 19/042; A61C 1/082
USPC ............................................. 606/172; 433/27
See application file for complete search history.

(56) References Cited

U.S. PATENT DOCUMENTS

| | | |
|---|---|---|
| RE43,328 E | 4/2012 | Foley et al. |
| 8,511,945 B2 | 8/2013 | Apkarian et al. |
| 2005/0116673 A1 | 6/2005 | Carl et al. |
| 2011/0264107 A1 | 10/2011 | Nikou et al. |
| 2013/0017507 A1 | 1/2013 | Moffson et al. |

OTHER PUBLICATIONS

Brady, et al. "The identification of bone regions for the assistance of temporal bone surgery through analysis of the drill acoustics." *Applied Sciences in Biomedical and Communication Technologies, 2009. ISABEL 2009. 2nd International Symposium on.* IEEE, 2009.

Shine, et al. "Digital spectral analysis of the drill-bone acoustic interface during temporal bone dissection: a qualitative cadaveric pilot study." *Otology & Neurotology* 27.5 (2006): 728-733.

SURGICAL TOOL MONITORING SYSTEM AND METHODS OF USE

CROSS-REFERENCE TO RELATED APPLICATIONS

This application is a divisional of U.S. patent application Ser. No. 14/496,704, filed Sep. 25, 2014, which claims the benefit of U.S. Provisional Application No. 61/882,223, which was filed on Sep. 25, 2013. The prior applications are incorporated herein by reference in their entirety.

FIELD

The present disclosure is directed to a surgical tool monitoring system and methods of using the same.

BACKGROUND

Neurosurgeons are required to perform meticulous drilling procedures in various regions of the skull without disturbing critical structures such as nerves, vessels, and most importantly the brain. When surgeons drill through the skull they carefully shave down the bone, layer by layer until they reach the dura, the thin protective covering of the brain compartment. This can be very time consuming as surgeons spend up to half an hour drilling through the final portions of bone because of the grave implications of drilling through the dura. One clue that neurosurgeons frequently use during a drilling procedure to ascertain the proximity of the drill to the dura are the drill sounds. The acoustical pitches generated by the vibrating bone have been observed to change as different bone layers are penetrated. In fact, many surgeons teach their trainees to listen specifically for these cues. Although the most experienced neurosurgeons are able to utilize these acoustical cues, the reality of human error compels these surgeons to drill slowly once a certain depth in the bone is reached.

Improvements in identifying the location of a drill relative to target areas of the patient's body are desirable to improve efficiency and accuracy of surgical procedures. In addition, improvements in identifying the physical state and condition of surgical tools are also desirable to ensure proper operation of those tools.

SUMMARY

Improvements on surgical techniques are always desirable to further improve the accuracy and efficiency of a surgical procedure. The systems and methods described herein provide systems for monitoring physical conditions (i.e., using one or more sensors) associated with a surgical tool to determine a state or condition of the surgical tool (i.e., proximity to various surfaces in the body and/or health of the surgical tool).

In some embodiments, a surgical tool is provided for cutting tissue in a body. The tool can comprise a cutting member, at least one sensor configured to provide information about at least one physical condition of the cutting member, and an indicator system that (1) receives the information obtained from the at least one sensor about the at least one physical condition of the cutting member, (2) analyzes the information to detect the approach of the cutting member to a transition from a first tissue type to a second tissue type, and (3) generates a first alert to a user when the cutting member is approaching the transition from the first tissue type to the second tissue type. The at least one sensor can comprise one or more microphones to obtain information about an acoustic state of the cutting member.

In some embodiments, the first tissue type comprises cortical bone and the second tissue type comprises dura mater. The indicator system can be configured to generate the first alert to a user when the cutting member is within 2 mm, or more preferably 1 mm, of the transition from the cortical bone to the dura mater.

Knowledge of impending penetration through bone that is near critical structures (e.g., nerves, nervous tissue, vessels, dura matter) can be particularly useful to a surgeon. However, it should be understood that the systems and methods described herein are also useful to detect transitions between other tissues types that is not adjacent to critical structures. In such events, the knowledge of impending transition between the tissue types is generally useful to the surgeon to reduce the risk of, for example, infection through contamination of the adjacent tissue and unnecessary trauma to the adjacent tissue—whatever that tissue may be. Accordingly, the systems and methods described herein can be useful in any surgical procedure in which a surgeon would desire an alert on an impending transition between tissue types.

In other embodiments, at least one accelerometer can be provided and the at least one physical condition of the cutting member also includes an acceleration state of the cutting member sensed by the at least one accelerometer. In other embodiments, at least one temperature sensor and the at least one physical condition of the cutting member also includes a temperature condition of the cutting member sensed by the at least one temperature sensor.

The system can also include a health indicator system. The health indicator system can be configured to receive the information obtained from the at least one sensor to determine a health condition of the cutting member and generate a second alert to the user regarding the health condition. The alerts provided by the system can include visual alerts, audible alerts, or both.

In one embodiment, the indicator system can be configured to receive initial information from the one or more microphones and modify the subsequent analysis of the information received by the one or more microphones based on this initial information. The initial information can include operational information about the acoustic state of the cutting member prior to contact with the tissue of the body.

In another embodiment, a method of identifying a state of a cutting tool during a surgical procedure is provided. The method includes contacting the cutting tool with tissue in a body, receiving information about a physical condition of the cutting tool from one or more sensors on the surgical tool as the cutting tool contacts the tissue, analyzing the received information and comparing the received information to stored information regarding predetermined states of the surgical tool to determine whether the cutting tool is approaching a transition between a first type of tissue and a second type of tissue, and based on the comparison, providing an indication to a user when the cutting member is approaching the transition from the first type of tissue to the second type of tissue. The at least one sensor can include one or more microphones and the physical condition of the cutting member can be an acoustic state of the cutting member.

In other embodiments, the method can include receiving initial information about the cutting tool prior to contact with the tissue from the one or more microphones and applying the received initial information to normalize the stored information regarding the predetermined states of the surgical tool. Instead of the originally stored information, or in addition to, the received information can be compared to the normalized stored information to determine whether the cutting tool is approaching a transition between a first type of tissue and a second type of tissue.

In other embodiments, the at least one sensor further comprises at least one accelerometer, and the received information about the physical condition of the cutting member further comprises an acceleration state of the cutting member. The at least one sensor can also further comprise at least one temperature sensor, and the received information about the physical condition of the cutting member further comprises a temperature state of the cutting member.

In some embodiments, the received information can be analyzed to determine a health condition of the cutting member and an indication can be generated about the health condition to the user. Indications can include alerts that convey information about the state of the cutting member to a surgeon, as a visual alert, audible alert, or both.

In one embodiment, the first type of tissue is cortical bone and the second type of tissue is dura mater. The indication that is provided to the user can be provided when the cutting member is within 2 mm of the transition from the cortical bone to the dura mater or, more preferably, when the cutting member is within 1 mm of the transition from the cortical bone to the dura mater.

The foregoing and other objects, features, and advantages of the invention will become more apparent from the following detailed description, which proceeds with reference to the accompanying figures.

BRIEF DESCRIPTION OF THE DRAWINGS

In FIG. 3, class 1 represents samples of background noise, class 2 represents samples of the drill running without making contact, class 3 represents drilling in contact with bone and without detection of dural noise, and class 4 represents drilling with detection of dural noise.

In FIG. 4, Class 1 represents samples from drills in good working order while class 2 represents drills that may be deteriorating.

FIG. 5 provides a binary classification of noise by combines class 1, 2, and 3 from FIG. 3 into class 1 of FIG. 5

DETAILED DESCRIPTION

Figure 1:
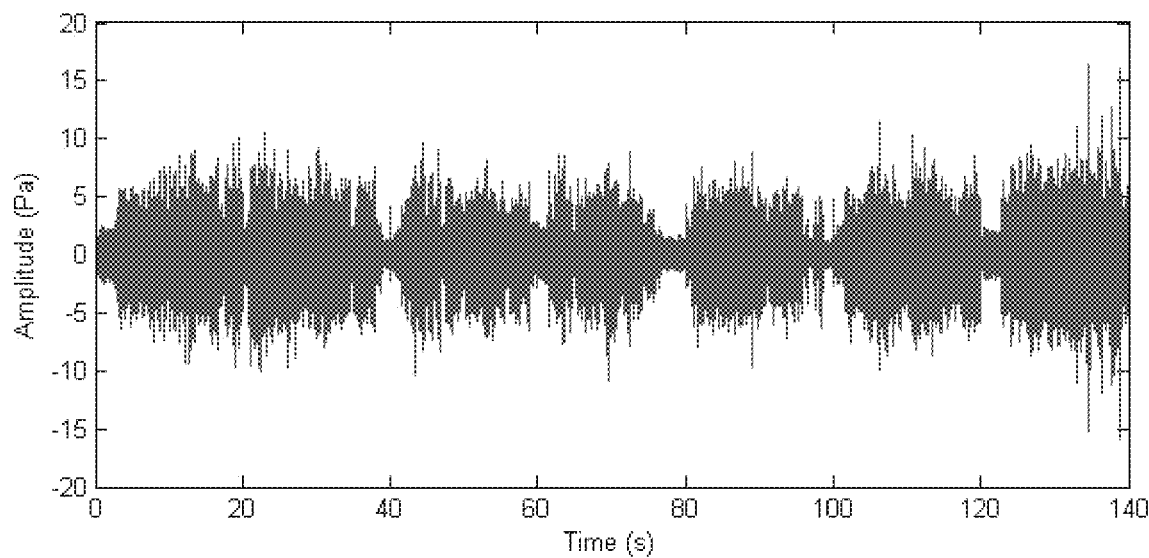
FIG. 1 is an example of an acoustic signal from a craniotomy.

The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the terms "a," "an," and "the" include both the singular and plural forms of the element(s) they refer to unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

As used herein, the term "dural noise" means acoustical events that are associated with a cutting member approaching a transition of cranial bone to dura mater before the penetration of the cutting member through the cranial bone.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

The following description relates to systems having sensors (e.g., accelerometers, microphones, temperature sensors, encoders, etc.) on surgical instruments for collection of relevant measurements such that the sensors provide information on the state of the instrument and its interaction with the patient, and methods of manufacturing and using the same. For example, in some embodiments, recording devices can record and analyze sounds from a tool used in a surgical procedure (i.e., a drill used in a drilling procedure) to developed a tool for reliably assessing proximity to the dural layer (and other areas of the body), as well as the condition (e.g., good/poor working condition) of the tool being used.

In some embodiments, the devices can utilize internal feedback from the instrument to provide information on the state of the instrument. As discussed herein, information about the state of the instrument can be conveyed to the user in various ways. The monitoring systems described herein can comprise aftermarket attachments to existing devices (e.g., drills, saws, ultrasonic bone cutters, and other bone-cutting instruments and powered instrumentations). Alternatively, they can be a self-contained system that is integrated with a particular instrument (e.g., drills, saws, ultrasonic bone cutters, and other bone-cutting instruments and powered instrumentations).

Methods of analyzing the collected data to extract information related to the instrument's condition and proximity to critical structures are provided herein. These methods can include, for example, Bayesian classifiers, neural networks, fuzzy logic, support vector machines, decision trees, etc.

In some embodiments, data can be collected from one or more sensors that are capable of providing information about the state of a device. For example, in one embodiment, a drill (e.g., a burr drill) was provided with various sensors to collect data corresponding to the drill during a surgical procedure, such as a craniotomy. In this example, accelerometers and microphones were used to record the output of burr drills used to perform craniotomies.

In some embodiments, an area of transition from a first type of tissue to a second type of tissue can be identified, and an indicator provided, before the cutting member passes through the first type of tissue. For neurosurgeons listening for changes in acoustical pitches, they are generally listening for change in sounds associated with cutting into a different type of material. However, in some embodiments, it can be more desirable to know that the transition is coming before the cutting member breaks through the first type of tissue and begins cutting the second type of tissue. It is, however, difficult to detect a pre-breakthrough event with conventional techniques.

Detecting the onset or approach of a transition area by passively monitoring acoustics associated with the contact of the cutting member and tissue can help prevent injury caused by plunge or loss of control upon breakthrough of the initial tissue layer. The skull generally comprises a first (outer) layer of cortical bone, a layer of cancellous bone, and a second (inner) layer of cortical bone. Detecting the onset of the transition through second layer of cortical bone in the skull and providing an indicator to alert the neurosurgeon that the cutting member is about to pass through the second layer of cortical bone can advantageously reduce plunge or loss of control of the cutting member and damage to dura mater adjacent the second layer of cortical bone.

As discussed in more detail below, it can be particularly desirable to identify when the transition from one tissue layer, such as the second layer of cortical bone, to another tissue layer, such as the dura mater, is less than about 2 mm from the current location of the cutting member (i.e., the tip of the cutting member) and, more preferably, when the transition is less than about 1 mm from the current location of the cutting member (i.e., the tip of the cutting member).

Example 1

An example of an acoustic signal recorded during a craniotomy on a cadaver head is shown in FIG. 1. These recorded signals were processed and metrics were developed that can aid in determining whether the drill was near the underlying soft tissue, or dura (critical structure). Such metrics come be developed using, for example, time- and frequency-domain signal processing techniques, as well as cepstral analysis. Included in the current set of metrics are power spectral density (PSD), PSD kurtosis, average power, cepstrum, signal-to-noise ratio, and others.

Figure 2:
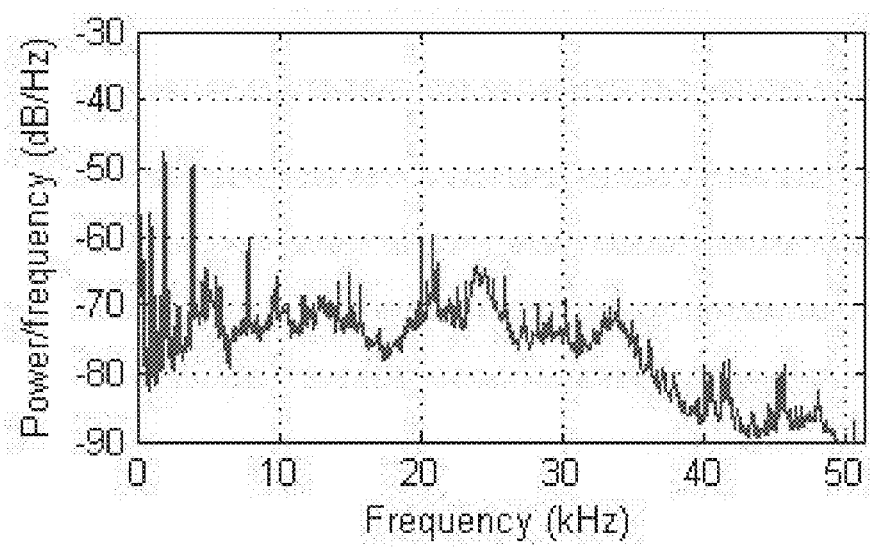
FIG. 2 is a power spectral density of an acoustic signal including dural contact.

An example power spectrum is shown in FIG. 2. One way to utilize these metrics is by training a classifier (e.g. an artificial neural network, a Bayesian classifier, etc.). Here, a neural network was used.

Figure 3:
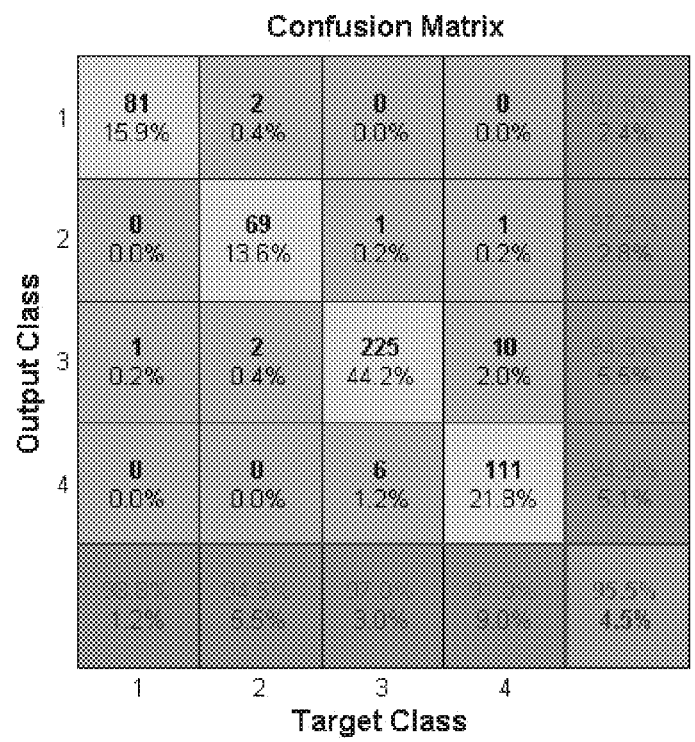
FIG. 3 is an example confusion matrix resulting from one iteration of the artificial neural network.
Figure 4:
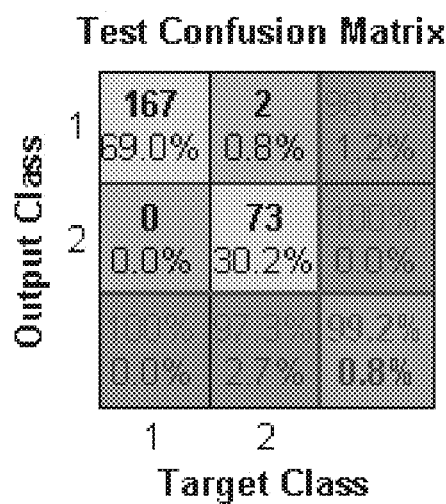
FIG. 4 is an example confusion matrix resulting from a neural network trained to classify the working order of surgical drills.
Figure 5:
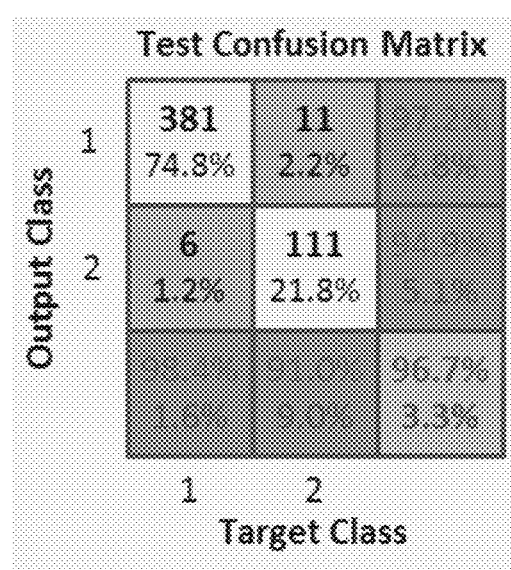
FIG. 5 is a simplified confusion matrix of that shown in FIG. 3.
Figure 6:
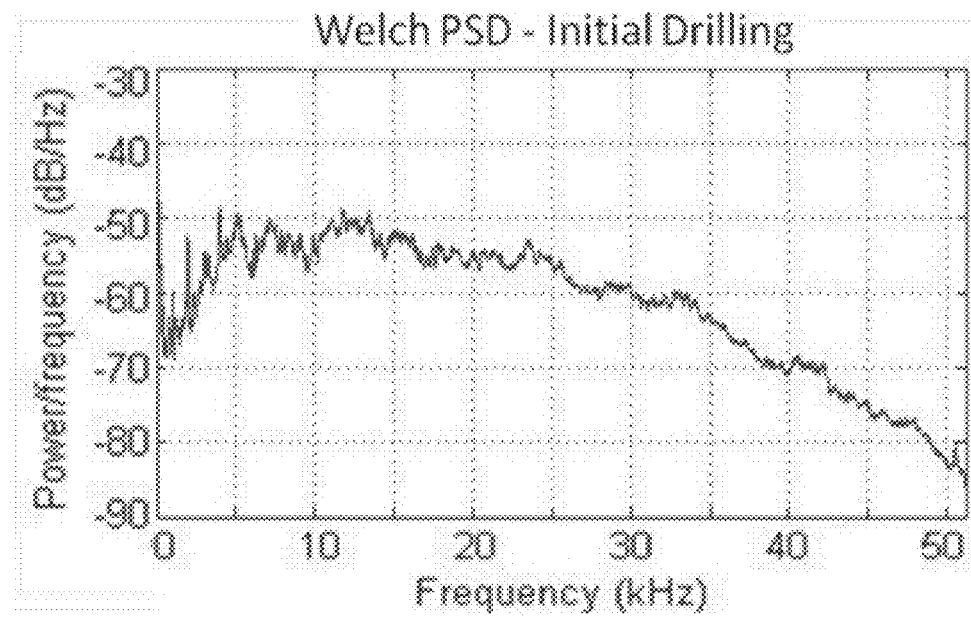
FIG. 6 is a power spectral density of an acoustic signal during an initial drilling (i.e., "free drilling" without contact).
Figure 7:
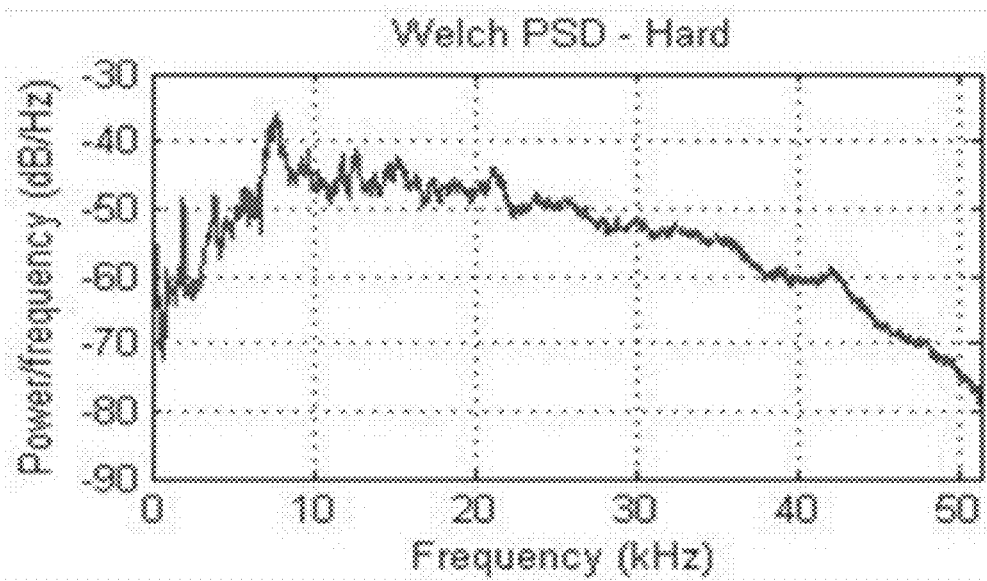
FIG. 7 is power spectral density of an acoustic signal while drilling the outer cortical bone.
Figure 8:
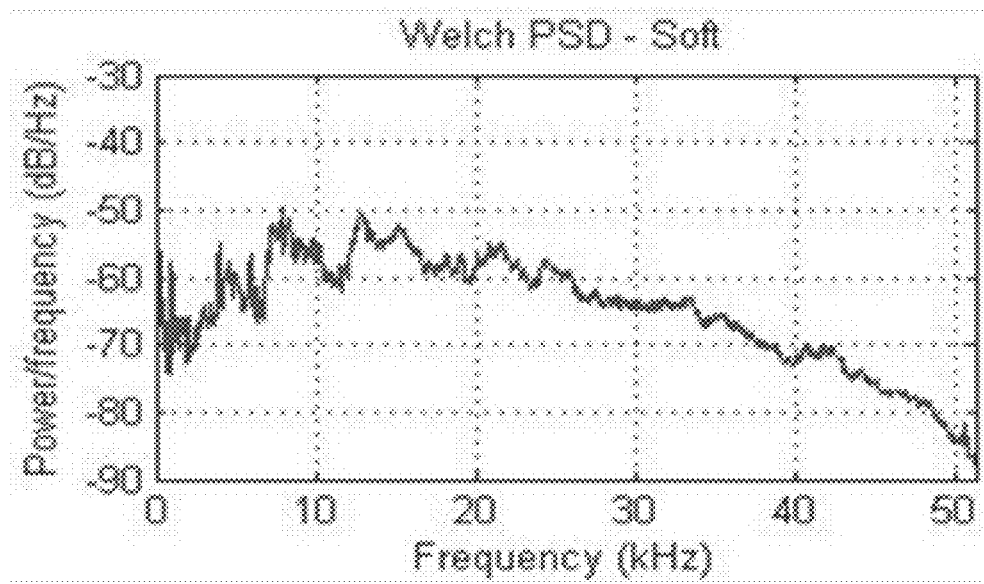
FIG. 8 is a power spectral density of an acoustic signal while drilling soft medullary bone.

Based on these metrics, an artificial neural network was developed with greater than 80% accuracy. The confusion matrix from one of these examples, shown in FIG. 3, shows the advantages of this technology. Here, classes 1-4 represent background noise, drill running without contact, drilling cranial bone without the presence of dural noise, and drilling with dural noise present (indicative of proximity to the underlying soft tissue), respectively. In this example, the classifier was able to correctly identify 110 of the 121 samples containing dural noise (class 4). Furthermore, of the 117 samples identified as containing dural noise, only 6 were false positives. FIG. 5 illustrates a simplified confusion matrix that illustrates a binary classification with Classes 1-3 of FIG. 3 combined into one class of noise (i.e., Class 1 of FIG. 4).

Using the same metrics, a similar neural network was trained to distinguish between deteriorating drills and drills in good working order. The data for this network was collected from a dozen surgical drills from two different brands. The confusion matrix in FIG. 4 shows the accuracy of the trained neural network. Here, class 1 represents samples from drills that run smoothly, and class 2 represents samples from drills that showed signs of deterioration (heat buildup, grinding, etc.). Out of 242 samples, only 2 were misclassified (99.2% overall accuracy).

Example 2

Experimental studies were performed on 8 cadaver heads. A microphone was placed approximately 1 foot from the drilling site to record data, and several holes were drilled at various locations in each cranium. A different fixed distance for microphone placement could also be used to record consistent data, or a variable distance may be compensated by some form of normalization as was done later in this effort.

In some embodiments, an accelerometer was also placed on the drill body near the forward bearing to record vibration data. The collected data were divided into clips about 0.5-1 second in length. These clips were manually categorized as one of 5 classes: (1) background noise; (2) free drilling (the drill was turned on but not in contact with bone); (3) contact between drill and bone without the dural noise; (4) possible dural noise; and (5) definite dural noise The result was a library of several thousand sound clips suitable for training and evaluating a classifier. The data may be divided into a different set of categories with the goal of characterizing the drill depth. For example, the following classes could be used to determine when a new layer of bone is reached: (1) background noise; (2) free drilling; (3) drilling of outer cortical bone, (4) drilling of medullary bone; (5) drilling of inner cortical bone; and (6) drilling near dura.

The number and definition of classes is not arbitrary but may be different than those presented here. Power spectral densities for these regimes are generally different, as shown in FIGS. 6-9. Spectra can be highly variable throughout drilling and from case to case, but the spectra shown in FIGS. 2, and 6-8 are generally representative of differences associated with free drilling (FIG. 6) and drilling different types of tissue, such as drilling at the outer cortical bone (FIG. 7), drilling at soft medullary bone (FIG. 8), and drilling near dura (FIG. 2).

For each of these spectra, the drill was operating at 60,000 RPM, or 1,000 Hz. Many of the harmonics at multiples of 1,000 Hz can be seen, particularly in FIG. 8, which illustrates the higher harmonics that are characteristic of spectra observed when drilling near dura mater. In some embodiments, frequency tracking algorithms, tachometers, and/or encoders are used.

Intraoperative data from 10 relevant surgeries was also collected. In order to preserve the sterile field, the microphone could usually be mounted no closer than 1 meter or so from the drilling site. To compensate for variations between surgeries (distance between drilling and sensors, variations in surgical equipment and technique, patient-dependent parameters, etc.), a normalization method was developed as described below. Both the experimental and intraoperative data were sampled at 50 kHz, although it is recognized that other sampling frequencies may be used to record more detail or reduce data storage.

Indicator Systems and Determining Onset of Tissue Transitions and Other Parameters In some embodiments, a direct determination of thresholds for particular sound characteristics can be used. Alternatively, the use of a classifier, as discussed below, allows the consideration of much more complex interactions between many metrics. Although other types of classifiers may be used, an artificial neural network (ANN) architecture was chosen for this work. In particular, a multilayer perceptron, consisting of 2 hidden layers with 50 neurons each, was trained with a back propagation algorithm. Other types of ANNs, such as radial basis function ANNs and self-organizing maps could be used. The dimensions of the input and output layers are determined by the number of metrics and categories, respectively, but the number and size of hidden layers may be chosen differently to change model complexity and accuracy. Supervised learning was used to train the ANN after data normalization, but other training methods (unsupervised, reinforcement learning, etc.) could be used as appropriate for a particular implementation of the device.

Aside from the choice of classifier architecture, the choice of metrics will affect the performance of the final device. Any number of metrics or combinations thereof may be selected and calculated for each training sample, but the chosen metrics included in one embodiment of the device were: (1) average acoustic power; (2) maximum power density in each harmonic band; (3) ratios of maximum power density in harmonic bands; (4) harmonic band kurtoses; (5) harmonic band kurtosis ratios; (6) normalized average power in harmonic bands; and (7) mel-scaled frequency cepstral coefficients.

The term "harmonic band" refers to a frequency band around a harmonic of the drill speed (in Hz) that need not be centered. Although some frequency-domain metrics may be calculated for the whole spectrum, others may be calculated based on partial spectrums, e.g. the energy in the spectrum for a harmonic band. For clarity, one particular implementation of each metric is discussed.

Average acoustic power may be calculated in the frequency domain from Parseval's Theorem/Welch's method and a Hamming window of length 4096 with 50% overlap are used to estimate the power spectral density (PSD) before integrating and averaging. Other methods, window types, and values of length and overlap may be used. Furthermore, instead of acoustic power, a generalized power may be calculated as is common in signal processing. If G(w) is the resulting single-sided PSD, then the average acoustic power is computed as:

$$\Pi = \int_0^{\omega_N} G(\omega) d\omega$$

where $\omega_N$ is the Nyquist frequency.

The maximum power density of each harmonic band may be calculated by using any method of PSD estimation, such as Welch's method above, then determining the maximum value in each harmonic band. The power of the partial spectrum, $\Pi_p$, in the desired harmonic band that ranges from the starting frequency of the harmonic band, $\omega_1$, to the end frequency, $\omega_2$, is:

$$\Pi = \int_{\omega_1}^{\omega_2} G(\omega) d\omega$$

In one embodiment, the harmonic bands were defined as 200 Hz wide with 75% of the band below the drill speed harmonic and 25% above. Any of these values may be adjusted. In fact, the size and shift of the harmonic bands may be chosen to vary with the harmonic number. Ratios, or other relationships, between these harmonic band power density maximums may also be used. Similarly, the harmonic bands may be used to calculate associated kurtoses of the PSD and their ratios. The kurtosis of the partial spectrum, $k_p$, is given by $$k_p = \frac{E[(|G(\omega)| - \mu)^4]}{\sigma^4}, \omega \in [\omega_1, \omega_2]$$

The kurtosis of the partial spectrum indicates the relative height of the drill harmonic above the noise floor. From FIG. 1, it can be seen that different drilling regimes produce harmonics of different heights. If the peak is high above the noise floor, a higher kurtosis will result and vice versa. While all harmonic band-based calculations may use the same harmonic band definition, it is conceivable that different definitions for different metrics may be beneficial.

Normalized average power, $\Pi_{N,p}$ in each harmonic band may be calculated in a similar manner to the average acoustic power except confined to a narrower frequency range. The normalization may include dividing the harmonic bands' average powers by the overall average power, or it may conceivably be carried out by normalizing with respect to one or more other metrics of the overall signal. Normalizing with respect to overall averaged power would be computed as:

$$\Pi_{N,p} = \frac{\Pi_p}{\Pi}$$

Normalization was found to greatly improved classifier accuracy from case to case, by providing better generalization from the ANN. Differences between cases include microphone and/or accelerometer different patients and different drill and/or burr types.

Finally, mel-scaled frequency cepstral coefficients (MFCCs) may be used as metrics by comparing the sample metrics to the mean values of reference data using a nearest neighbor approach rather than a more complex machine learning architecture.

With metrics calculated, a classifier can be trained to model the n-dimensional boundaries between classes. To aid in this process, the metrics are sometimes mapped to a smaller range of values. Besides this, the metrics in this effort may be normalized with respect to the average feature values of a subset of a particular class within the same experiment/case. For example, in a particular surgery, the data metrics may be normalized by the average values obtained during the first 10 seconds of the "free drilling" class. This allows the system to account for differences that might arise from case to case (microphone and/or accelerometer placement, surgical tools and technique, patient-dependent parameters, etc.). This is different than mapping in that the normalization depends on the incoming signal rather than a static map or an overall average value even after training the classifier; however, this method also differs from common normalizations as it depends on the classifier output as well.

Figure 9:
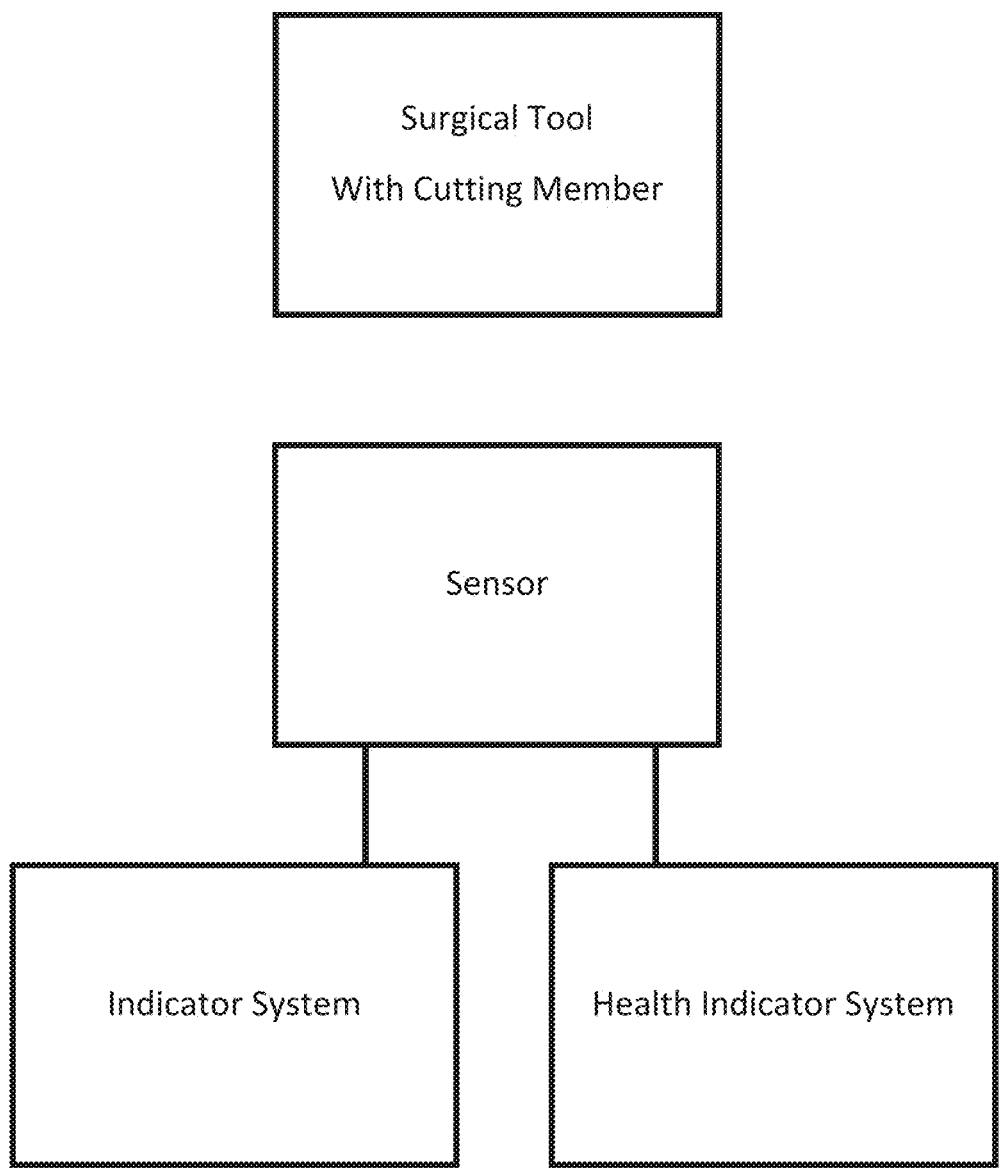
FIG. 9 is a schematic representation of a surgical tool system.

Based on the output of the analyses discussed above, the devices disclosed herein can alert the surgeon to the operating conditions of the drill (i.e., status of drill health, drill location in patient, etc.). As shown in FIG. 9, an indicator system can be provided that receives the information obtained from the sensor(s) about the physical condition(s) of the cutting member (e.g., location or heath condition of cutting member), analyzes the information to detect the relevant information (e.g., the approach of the cutting member to a transition from a first tissue type to a second tissue type or the health of the cutting member), and generates an alert to a user about the monitored condition.

To process the information received from the sensor(s), the indicator system can comprise one or more microprocessors coupled to the sensors, as well as memory to store the information and/or results of the analyses discussed herein. One of ordinary skill in the art would understand that any conventional processors and computing systems can be programmed to receive the information and perform the comparative analyses and alert-generating steps described herein.

Thus, for example, based on an analysis of the output of one or more sensors, the device can determine whether the drill is nearing a critical structure and, if so, provide an alert (e.g., sound an alarm and/or alter a display). Similarly, based on an analysis of the output of one or more sensors, the device can alert the surgeon when a drill is performing outside of a predetermined quality condition (i.e., when the drill is no longer in good working order). If the device is in poor working order, an alert can be provided so that the drill can be replaced if necessary to reduce the risk of complications during surgery (e.g., patient injury and/or extended OR time). Outside of actual surgery, the device could also be used diagnostically for maintenance purposes, and hospitals would be better able to handle their equipment inventory in an efficient manner.

The sensors described herein can be positioned in various locations. For example, microphones associated with a cutting tool can be located at a position near the cutting surface of the cutting tool and/or spaced apart from the cutting surface by a meter or more. If the location of the microphones are not fixed relative to the cutting surface of the cutting tool, the normalization step discussed above (i.e., obtaining information about an initial free drilling state) can improve operation by reducing acoustic differences that may result from different placements of the microphones relative to the cutting surface.

The methods and systems described herein provide numerous advantages over conventional equipment. For example, such systems and methods can enable surgeons to reduce risk to a patient during surgery by improving accuracy and shortening the duration of surgery. In some cases, for example, a surgery might be able to be reduced by about 15-30 minutes.

The systems and method described herein can also be directly applied to surgery applications that utilize robotic systems to aid in surgical procedures. In such systems, in addition to, or instead of, providing the user with an alert about the approach of the cutting tool to a transition between tissue types, the alert or information can be provided to the control system of the robotic system and the robotic system can be configured to respond accordingly. Thus, for example, when an alert or information is provided to the control system that the tissue transition is approaching, the control system can respond—like the surgeon would—by either slowing or stopping the operation of the cutting tool.

With a reliable indicator of proximity to critical structures, even inexperienced surgeons will be able to drill faster and more dependably, reducing the time of the surgery which can reduce both risk to the patient and cost of the procedure.

Furthermore, a prognosis for useful drill life will enable hospitals to handle equipment maintenance and replacement more efficiently while reducing the risk of equipment failure during surgery. Surgical drills can cost hundreds of dollars. Without a method of estimating remaining life, hospitals are forced to have redundant equipment on hand and conduct unnecessary routine maintenance to ensure they will not be without a working drill.

In some embodiments, additional alerts or controls can be provided based on parameters associated with the operation of the cutting tool. For example, the system can provide a control system that alters or overrides the operation of the cutting tool when certain conditions are met. In one example, the control system can slow down or stop operation of the cutting tool when it is detected that the cutting tool has been in a particular region for a period of time that exceeds a predetermined amount of time. In this manner, for example, the fact that the cutting tool remains within a first region of tissue (e.g., cortical bone) for an extended period of time may indicate a problem in either the operation of the cutting tool or with the patient, and slowing down the cutting tool or stopping the cutting tool may prevent aggravation of the problem.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of identifying a state of a cutting tool during a surgical procedure, the method comprising:
   contacting the cutting tool with tissue in a body;
   receiving condition information about a physical condition of the cutting tool from one or more sensors on the cutting tool as the cutting tool contacts the tissue;
   analyzing the received condition information and comparing the received condition information to stored information regarding predetermined states of the cutting tool to determine whether the cutting tool is approaching a transition between a first type of tissue and a second type of tissue; and
   based on the comparison, providing an indication to a user when the cutting tool is approaching the transition from the first type of tissue to the second type of tissue;
   wherein the one or more sensors comprise one or more microphones and the physical condition of the cutting member comprises an acoustic state of the cutting tool,
   wherein the method further comprises:
   receiving initial information about the cutting tool prior to contact with the tissue from the one or more microphones;
   applying the received initial information to normalize the stored information regarding the predetermined states of the cutting tool; and
   comparing the received information to the normalized stored information to determine whether the cutting tool is approaching the transition between the first type of tissue and the second type of tissue.

2. The method of claim 1, wherein the one or more sensors further comprise at least one accelerometer, and the received condition information about the physical condition of the cutting tool further comprises an acceleration state of the cutting member.

3. The method of claim 1, wherein the one or more sensors further comprise at least one temperature sensor, and the received condition information about the physical condition of the cutting tool further comprises a temperature state of the cutting member.

4. The method of claim 1, further comprising:
analyzing the received condition information to determine a health condition of the cutting tool; and
generating an indication about the health condition to the user.

5. The method of claim 1, wherein the indication comprises an alert that conveys status information about the state of the cutting tool to a surgeon.

6. The method of claim 5, wherein the alert comprises a visual alert, audible alert, or both a visual and audible alert.

7. The method of claim 1, wherein the first type of tissue is cortical bone and the second type of tissue is dura mater.

8. The method of claim 7, wherein the indication is provided to the user when the cutting tool is within 2 mm of the transition from the cortical bone to the dura mater.

9. The method of claim 7, wherein the indication is provided to the user when the cutting tool is within 1 mm of the transition from the cortical bone to the dura mater.

10. A method of identifying a state of a cutting tool during a surgical procedure, the method comprising:
contacting the cutting tool with tissue in a body;
receiving condition information about a physical condition of the cutting tool from one or more sensors on the cutting tool as the cutting tool contacts the tissue;
analyzing the received condition information and comparing the received condition information to stored information regarding predetermined states of the cutting tool to determine whether the cutting tool is approaching a transition between a first type of tissue and a second type of tissue; and
based on the comparison, providing an indication to a user when the cutting member is approaching the transition from the first type of tissue to the second type of tissue;
wherein the one or more sensors comprise one or more microphones and the physical condition of the cutting member comprises an acoustic state of the cutting tool, and
wherein the first type of tissue is cortical bone and the second type of tissue is dura mater.

11. The method of claim 10, wherein the one or more sensors further comprise at least one accelerometer, and the received condition information about the physical condition of the cutting tool further comprises an acceleration state of the cutting member.

12. The method of claim 10, wherein the one or more sensors further comprise at least one temperature sensor, and the received condition information about the physical condition of the cutting tool further comprises a temperature state of the cutting member.

13. The method of claim 10, further comprising:
analyzing the received condition information to determine a health condition of the cutting tool; and
generating an indication about the health condition to the user.

14. The method of claim 10, wherein the indication comprises an alert that conveys status information about the state of the cutting tool to a surgeon.

15. The method of claim 14, wherein the alert comprises a visual alert, audible alert, or both a visual and audible alert.

16. The method of claim 10, wherein the indication is provided to the user when the cutting tool is within 2 mm of the transition from the cortical bone to the dura mater.

17. The method of claim 10, wherein the indication is provided to the user when the cutting tool is within 1 mm of the transition from the cortical bone to the dura mater.

* * * * *